United States Patent [19]

Hillier et al.

[11] 4,048,254

[45] Sept. 13, 1977

[54] BLEND OF THERMOPLASTIC POLYMERS WITH BLOCK RADIAL BUTADIENE-STYRENE POLYMERS

[75] Inventors: Edward Lawrence Hillier; Glen Henry Graham; Warren Evan Eichelberger, all of Ashland, Ohio

[73] Assignee: Abbott Laboratories, North Chicago, Ill.

[21] Appl. No.: 607,978

[22] Filed: Aug. 26, 1975

[51] Int. Cl.² .................. C08L 27/00; C08L 51/00
[52] U.S. Cl. .................. 260/859 R; 260/33.6 UA; 260/33.6 UB; 260/857 G; 260/857 D; 260/873; 260/876 B; 128/214 R
[58] Field of Search .................. 260/876 B, 859 R

[56] References Cited

U.S. PATENT DOCUMENTS

| 3,562,355 | 2/1971 | Holden | 260/859 |
| 3,646,161 | 2/1972 | Marwede et al. | 260/876 B |
| 3,686,365 | 8/1972 | Sequeira | 260/876 B |
| 3,753,936 | 8/1973 | Marrs | 260/27 R |

Primary Examiner—Richard B. Turer
Attorney, Agent, or Firm—Robert L. Niblack; Neil F. Hamilton

[57] ABSTRACT

Radial block copolymers are mechanically combined with additional polymeric materials to form plastic compositions having a high degree of clarity so that they can be substituted for polyvinylchloride plastic compositions in the fabrication of such devices as intravenous and blood tubing, containers for intravenous solutions and blood fractions, functional parts of intravenous administration equipment such as sight and drip chambers, needle adapters and miscellaneous assemblies for contact with intravenous fluids. The compounds of this invention can also be utilized for catherization, bodily drainage systems, and as pharmaceutical closures, resealable injection sites and syringe plunger tips.

22 Claims, No Drawings

BLEND OF THERMOPLASTIC POLYMERS WITH BLOCK RADIAL BUTADIENE-STYRENE POLYMERS

BACKGROUND OF THE INVENTION

This invention relates to thermoplastic polymers which are useful in molding plastic materials for contact with body fluids. More particularly, it relates to a thermoplastic polymer composed of block radial polymers of the diene-aryl substituted olefin butadiene-styrene type which have blended with them certain polymeric materials to form a plastic composition having a high degree of clarity which are particularly useful in extruding or molding tubing, drip chambers and other components useful in the field of parenteral administration.

Recently, radial block polymers of the diene-aryl substituted olefin butadiene-styrene type have been of particular interest in that they display high tensile strength without vulcanization or filler reinforcement. These copolymers can be processed on conventional plastics or rubber equipment without the addition of plasticizers. In U.S. Pat. Nos. 3,281,383 and 3,078,254, processes for making such radial block copolymers are described. Further, particular blends of vulcanized butadiene-styrene block copolyers are indicated in U.S. Pat. No. 3,646,161. In U.S. Pat. No. 3,562,355, a mechanical blend of a butadiene-styrene copolymer is described in combination with a polyester urethane. The prior art nowhere describes a blend of nonvulcanized radial block copolymers of the butadiene-styrene type wherein the butadiene-styrene amounts are of a certain minimum quanity so that when they are combined with certain polymeric materials, they will form a plastic composition having a sufficient clarity, hardness, tensile strength and elongation to be readily adaptable for use in composing plastic materials for contact with parenteral fluids. In addition, the prior art nowhere describes a plastic composition which is readily suitable for use in the medical plastics field which will have low alkaline extraction values so that ingredients in the composition are not extracted into the fluids to be administered.

It is an advantage of the present invention to provide a novel blend of radial block copolymers of the butadiene-styrene type with other polymeric materials. Other advantages are a thermoplastic composition of the radial block copolymer type which have a high degree of clarity so that they can replace polyvinylchloride as a material in the forming of medical plastic product such as tubing, drip chambers, injection reseal device and other parenteral administration equipment, a novel radial block copolymer mixture which can be readily molded, extruded and otherwise processed by customary processes, a thermoplastic material which is compatible with the usual plasticizers, fillers, chelators, lubricants, etc. which are necessary in the fabrication of plastic materials.

SUMMARY OF THE INVENTION

The foregoing advantages are accomplished and the shortcomings of the prior art are overcome by the present radial block copolymer mixture which is composed of from about 10 – 90% by weight of a butadiene-styrene radial block copolymer having a butadiene content in the range of about 85 – 60% by weight and a styrene content in the range of about 15 – 40% by eight, from about 90 – 10% by weight of a butadiene-styrene radial block copolymer having differing butadiene contents in the range of about 85 – 60% by weight and a styrene content in the range of about 15 – 40% by weight and 5 – 75% by weight of the radial block copolymer of certain polymeric or copolymeric materials such as acrylics, thermoplastic epoxides, styrene acrylonitrile, polycarbonates, polybutenes and polyisobutylenes, polyesters, polyolefins, polystyrenes, polyvinylchloride and olefin/P.V.C. copolymers, polyether and polyester urethane polymers and methacrylate-styrene-butadiene copolymers and mixtures thereof. Of the foregoing those preferred are thermoplastic polyether urethane polymers, methyl methacrylate-styrene-butadiene copolymers, methyl methacrylate-acrylonitrile-styrene-butadiene copolymers and thermoplastic polyester urethane polymers, and mixtures thereof. In a preferred composition, one of the radial block copolymers has a butadiene content of about 70 by weight and a styrene content of 30% by weight and the other butadiene-styrene copolymer has a butadiene content of about 60% by weight and a styrene content of about 40% by weight with the copolymer having the 70:30 butadiene-styrene ratio present in an amount in the range of about 90 – 45% by weight with the polymer having the 60:40 butadiene-styrene ratio present in the range of about 10 – 55% by weight with a 75 to 25% ratio preferable.

Description of the Preferred Embodiment

In the following Examples, certain polymers, plasticizers, chelators, lubricants, antioxidants, etc. are referred to in composing the novel compositions of this invention. All of the materials are readily available on the commercial market and a brief explanation of them is given:

| Product | Trade Name | Source |
| --- | --- | --- |
| Polymers | | |
| Radial block copolymer (70:30 butadiene-styrene) | Solprene 411 | Phillips Petroleum Co. |
| Radial block copolymer (60:40 butadiene-styrene) | Solprene 414 | Phillips Petroleum Co. |
| Butadiene-styrene-methyl methacrylate polymer | Acryloid KM-636 | Rohm & Haas Co. |
| Thermoplastic polyether urethane | Roylar E-85 | Uniroyal Chemical Co., Division of Uniroyal, Inc. |
| Butadiene-styrene-methyl methacrylate polymer | Acryloid KM-641 | Rohm & Haas Co. |
| Butadiene-styrene-methacrylate-acrylonitrile polymer | Blendex 435 | Marbon Division, Borg-Warner Corp. |
| Thermoplastic polyether urethane polymer | Roylar E-80 | Uniroyal Chemical Co., Division of Uniroyal, Inc. |
| Thermoplastic polyester urethane polymer | Estane 5701 | B. F. Goodrich Chemical Co., Division of B. F. Goodrich |
| Processing Aid | | |
| Acrylic processing aid | Acryloid K-175 | Rohm & Haas Co. |
| Plasticizers | | |
| Monomeric epoxy | Epoxol 8-2B | Swift Chemical Co., Division of Swift and Company |
| Mineral oil U.S.P. grade | — | An available |
| Chelator | | |
| Tris nonyl phenyl phosphite | Mark 1178 | Argus Chemical Co., Division of |

-continued

| Product | Trade Name | Source |
|---|---|---|
| Lubricants | | Witco Chemical Co. |
| Mono fatty acid ester of fatty alcohols | Loxiol G-40 | Henkel, Inc. |
| Diglyceryl ester of unsaturated fatty acids | Loxiol G-16 | Henkel, Inc. |
| Complex ester of unsaturated fatty acids | Loxiol G-71 & G-73 | Henkel, Inc. |
| Antioxidants | | |
| Octadecyl 3-(3',5' ditert-butyl-4'-hydroxyphenyl) propionate | Irganox 1076 | Ciba-Geigy |
| 2,4 ditert.-p-butyl cresol | Ionol CP | Shell Chemical Co. |
| Tetrakis-[methylene-3-(3',5' di-t-butyl-4'-hydroxyphenyl)propionate] methane | Irganox 1010 | Ciba-Geigy |

The invention is disclosed in further detail by means of the following Examples which are set forth for the purpose of illustrating the invention, but, in no way are to be construed as limiting the invention to the precise amounts, ingredients or conditions indicated.

Example I

| Ingredients | Formula by Parts | % Comp. |
|---|---|---|
| Radial block copolymer (70:30 butadiene-styrene) | 75.0 | 58.73 |
| Radial block copolymer (60:40 butadiene-styrene) | 25.0 | 19.58 |
| Butadiene-styrene-methyl methacrylate polymer (Acryloid KM-636) | 10.0 | 7.83 |
| Thermoplastic polyether urethane polymer (Roylar E-85) | 10.0 | 7.83 |
| Monomeric epoxy plasticizer | 5.0 | 3.91 |
| Chelator (tris nonyl phenyl phosphite) | 0.5 | 0.39 |
| Lubricant (mono fatty acid ester of fatty alcohols) | 2.0 | 1.57 |
| Antioxidant (octadecyl 3-(3',5' ditert.-butyl-4-hydroxyphenyl)propionate) | 0.2 | 0.16 |
| | 127.7 | 100.00 |

The proper amount of ingredients are weighed out and placed in a low shear blender such as a Prodex-Henschel or a ribbon blender. The ingredients are mixed at a low speed for approximately five minutes to assure a good, dry blend. The resulting finished compound can then either be stored in proper containers for future use in extrusion, injection molding, transfer molding, etc. For tubing extrusion in a 2 or 2¼ inch 24/1 L/D extruder, the compound is placed in a hopper and extruded using a single stage screw with heat zones between 300° – 400° F. Tubing was extruded at a rate of 100 feet per minute and had an internal diameter of 0.100 inch and an outside diameter of 0.138 inch. The tubing was extruded in 3,000 foot lengths. For best transfer molding results, the compounds should be fused first into a slab form. The compound can also be injection molded as a dry blend or in pellitized form. Typical properties for the resulting material when fabricated as a female needle adapter with luer fittings at one end and a tubing connector sleeve at the other end or as an I.V. bag reseal were as follows:

| Clarity | Shore "A" Durometer | 100 % Modulus | Ultimate Tensile | Ultimate % Elongation |
|---|---|---|---|---|
| +5 | 74 | 300 | 1875 | 697 |

Example II

| Ingredients | Formula by Parts | % Comp. |
|---|---|---|
| Radial block copolymer (70:30 butadiene-styrene) | 75.0 | 67.10 |
| Radial block copolymer (60:40 butadiene-styrene) | 25.0 | 22.40 |
| Butadiene-styrene-methyl methacrylate polymer (Acryloid KM-641) | 10.0 | 9.00 |
| Chelator (tris nonyl phenyl phosphite) | 0.5 | 0.40 |
| Lubricant (diglyceryl ester of unsaturated fatty acids) | 1.0 | 0.90 |
| Antioxidant (tetrakis-[methylene-3-(3',5'-di-t-butyl-4'-hydroxyphenyl)propionate] methane) | 0.2 | 0.17 |
| | 111.7 | 100.00 |

The mixing and molding procedures were the same as in Example I and a product when fabricated into tubing having the same internal and outside diameters had the following:

| Clarity | Shore "A" Durometer | 100 % Modulus | Ultimate Tensile | Ultimate % Elongation |
|---|---|---|---|---|
| +3 | 75 | 358 | 3292 | 673 |

Example III

| Ingredients | Formula by Parts | % Comp. |
|---|---|---|
| Radial block copolymer (70:30 butadiene-styrene) | 75.0 | 65.96 |
| Radial block copolymer (60:40 butadiene-styrene) | 25.0 | 22.00 |
| Butadiene-styrene-methacrylate-acrylonitrile polymer | 10.0 | 8.79 |
| Monomeric epoxy plasticizer | 2.0 | 1.76 |
| Chelator (tris nonyl phenyl phosphite) | 0.5 | 0.44 |
| Lubricant (mono fatty acid ester of fatty alcohols) | 1.0 | 0.88 |
| Antoxidant (2,4 ditert.-p-butyl cresol) | 0.2 | 0.17 |
| | 113.7 | 100.00 |

The mixing and molding procedures were the same as in Example I. The typical properties for a product when fabricated into the same size of tubing were as follows:

| Clarity | Shore "A" Durometer | 100 % Modulus | Ultimate Tensile | Ultimate % Elongation |
|---|---|---|---|---|
| +3 | 77 | 400 | 3017 | 657 |

Example IV

| Ingredients | Formula by Parts | % Comp. |
|---|---|---|
| Radial block copolymer (70:30 butadiene-styrene) | 75.0 | 65.96 |
| Radial block copolymer (60:40 butadiene-styrene) | 25.0 | 22.00 |
| Thermoplastic polyether urethane polymer (Roylar E-80) | 10.0 | 8.79 |
| Monomeric epoxy plasticizer | 2.0 | 1.76 |
| Chelator (tris nonyl phenyl phosphite) | 0.5 | 0.44 |
| Lubricant (complex ester of unsaturated fatty acids, Loxiol G-71) | 1.0 | 0.88 |
| Antioxidant (2,4 ditert.-p-butyl cresol) | 0.2 | 0.17 |
|  | 113.7 | 100.00 |

The mixing and molding procedures were the same as in Example I and the typical properties for a product when fabricated into the same size tubing and 13 and 20 mm. bottle closures were as follows:

| Clarity | Shore "A" Durometer | 100 % Modulus | Ultimate Tensile | Ultimate % Elongation |
|---|---|---|---|---|
| +4 | 75 | 350 | 3233 | 700 |

Example V

| Ingredients | Formula by Parts | % Comp. |
|---|---|---|
| Radial block copolymer (70:30 butadiene-styrene) | 75.0 | 66.55 |
| Radial block copolymer (60:40 butadiene-styrene) | 25.0 | 22.18 |
| Thermoplastic polyester urethane polymer | 9.0 | 7.99 |
| Monomeric epoxy plasticizer | 2.0 | 1.77 |
| Chelator (tris nonyl phenyl phosphite) | 0.5 | 0.44 |
| Lubricant (diglyceryl ester of unsaturated fatty acids) | 1.0 | 0.89 |
| Antioxidant (2,4 ditert.-p-butyl cresol) | 0.2 | 0.18 |
|  | 112.7 | 100.00 |

The mixing and molding procedures were the same as in Example I and the typical properties for a product when fabricated into the same size of tubing and flexible Y reseal for I.V. sets were as follows:

| Clarity | Shore "A" Durometer | 100 % Modulus | Ultimate Tensile | Ultimate % Elongation |
|---|---|---|---|---|
| +4 | 78 | 367 | 3175 | 697 |

Example VI

| Ingredients | Formula by Parts | % Comp. |
|---|---|---|
| Radial block copolymer (70:30 butadiene-styrene) | 37.5 | 23.78 |
| Radial block copolymer (60:40 butadiene-styrene) | 12.5 | 7.93 |
| Butadiene-styrene-methyl methyacrylate polymer (Acryloid KM-641) | 100.0 | 63.40 |
| Acrylic processing aid | 3.0 | 1.90 |
| Lubricnt (complex esters of unsaturated fatty acids, Loxiol G-73) | 2.0 | 1.27 |
| Chelator (tris nonyl phenyl phosphite) | 0.5 | 0.32 |
| Antioxidant (2,4 ditert.-p-butyl cresol) | 0.2 | 0.13 |
| Plasticizer (mineral oil, U.S.P. grade) | 2.0 | 1.27 |
|  | 157.7 | 100.00 |

The mixing and molding procedures were the same as in Example I and the typical properties for these ingredients when molded into a semirigid luer type needle adapter and sight chamber were as follows:

| Clarity | Shore "A" Durometer | 100 % Modulus | Ultimate Tensile | Ultimate % Elongation |
|---|---|---|---|---|
| +2 | 80 | 800 | 2300 | 450 |

Concerning the composition in Example VI, it should be pointed out that the clarity of this compound can be improved by using a different butadiene-styrene-methyl methacrylate polymer or butadiene-styrene-methyl mehacrylateacrylonitrile polymer and eliminating the acrylic processing aid or making a lubricant substitution.

In the preceding Examples and following Table I, certain tests are referred to for the thermoplastic products formed by this invention. They are described as follows:

"Clarity" — A grading using plasticized polyvinylchloride as a comparative control of +5.

The 100% Modulus, Ultimate Tensile and Ultimate % Elongation were obtained using ASTM Test Method: D-142-66 using a Type C die and an Instron Tensile Tester.

a. 100% Modulus is the force required to elongate the dumbbell-shaped sample 100% using a one-inch bench mark for reference.

b. Ultimate Tensile is the force per cross-sectional area required to pull the sample apart.

c. % Elongation is the elongation of the sample at break. A one-inch bench mark is placed on the sample before elongation. Then the distance between the marks at break minus one inch times 100 gives the percent elongation.

Shore A Durometer is a procedure for determining indentation hardness of materials (ASTM-D-2240). The method is based on a specified indentor forced into the material under specified conditions.

In the following Examples I and IV, a thermoplastic polyether urethane polymer was referred to. These polymers are the linear reaction products of polyether glycols and aromatic diisocyanates. In addition to being clear, they are especially suitable for forming reseal devices such as injection sites and pierceable stoppers because of their elastomeric properties. The urethane polymers of the thermoplastic polyester type utilized in Example V are the reaction products of linear hydroxyl terminated aliphatic polyesters, an aromatic diisocyanate and an aliphatic diol. Further, methyl methacrylate-styrene-butadiene copolymers are indicated for use with the blend of the radial block styrene-butadiene copolymers as well as methyl methacrylate-acrylonitrile-styrene-butadiene copolymers. Other polymers or copolymers which could be utilized and still provide a degree of clarity with the basic blend of radial block copolymers would be those which will impart unique properties such as hot strength and resistance to cold flow; will be compatible at working levels; can be used in nontoxic applications; will process at 300° – 400° F. in the compound. These would include the following polymers or copolymers: acrylics, thermoplastic epoxies, polycarbonates, and polyisobutylenes, polyesters, polyvinylchloride and olefin/P.V.C. copolymers.

Certain components are utilized as being fabricated from the radial block copolymer mixture of this invention. Others would include various types of closures such as pharmaceutical closures, flexible containers, syringe plunger tips and elastomeric bulbs.

Certain amounts of the polymeric materials in relation to the combined weight of the radial block copolymers are indicated in the Examples. These amounts can be adjusted and still provide the advantages of this invention. For example, the amount of the methyl methacrylate-styrene-butadiene copolymers can be present in an amount in the range of about 5 parts by weight to about 200 parts by weight per 100 parts by weight of the combined radial block copolymers; the polyether urethane in an amount in the range of about 10 to about 50 parts by weight per 100 parts by weight of the combined radial block copolymers; the polyester urethane in an amount not exceeding 50 parts by weight; and the methyl methacrylateacrylonitrile-butadiene-styrene in an amount in the range of about 10 to about 70 parts per 100 parts by weight of the radial copolymers.

Plasticizers may be incorporated into the foregoing compositions in varying concentrations in amounts of about 2 to about 50 parts by weight per 100 parts by weight of the combined radial block copolymers. These plasticizers would be those sanctioned for use by the U.S. Food and Drug Administration. The preferred choices are U.S.P. grade mineral oil and monomeric epoxidized esters in low concentrations, i.e. less than 10% by weight. Of course chelators, lubricants, antioxidants, pigments and fillers, may be incorporated into these compositions in required concentrations. As indicated in the Examples, the compositions may be mixed or blended by conventional plastics or rubber methods. For example, mixing may be done by simple tumbling, intensive mixers, open mill mixing, Banbury mixing or by extrusion and pelletizing or dicing. The resulting product can be of various shapes and configurations such as plastic tubing or a drip chamber.

The Table shows the properties obtained with twenty radial block copolymer combinations of differing butadiene-styrene contents. Conclusions and applications which can be made from this data are:

1. The Short A durometer increases with the higher styrene content. Higher durometers are suitable for plastics molded parts, whereas lower durometers are favored for closures.

2. Tensile strength increases with styrene content and preferred ranges lie above 25% styrene content.

3. Ultimate elongation shows a desired maxima between 25 and 37% styrene content.

4. One-hundred percent modulus increases with styrene content. Higher values above 30% styrene content are desired for plastics usage in tubing and plastics molded parts. Lower values, below 30% styrene, would be desirable in closure applications.

5. Alkaline extraction decreases with increaed styrene content. It is desired to obtain the lowest values.

6. Optimum clarity is found between 25 – 35% styrene content.

It should be pointed out that in all of twency radial block copolymer formulations the additional polymers and additives employed in conjunction with the radial block copolymers are the same and are illustrated in the previous Examples. It will also be seen from the Table that the preferred average molecular weight of the blend of the radial block copolymers is between 150,000 and 270,000.

It will thus be seen that through the present invention there is provided a novel plastic composition which through its physical characteristics can be utilized to compose various components for administering fluids to the body. The composition has a high degree of clarity yet can be processed by various plastic and rubber fabricating techniques. Most importantly, the compositions have very low extraction values which makes them especially suitable for use in handling parenteral solutions.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

TABLE I

| | | Molec. Wt. × 1,000 | 1 | 2 | 3 | 4 | 5 | 6 | 7 | 8 | 9 | 10 |
|---|---|---|---|---|---|---|---|---|---|---|---|---|
| Radial Block Copolymer | A | 300 | 100 | | | | | | 77.4 | 48 | 33 | 77.4 |
| | B | 150 | | 100 | | | | 75 | | 52 | 67 | |
| | C | 150 | | | | | | 25 | | | | |
| | D | 150 | | | 100 | | | | 22.6 | | | 22.6 |
| | E | 150 | | | | 100 | | | | | | |
| | F | 250 | | | | | 100 | | | | | |
| Additional Polymers and Additives | | | 27.7 | 27.7 | 27.7 | 27.7 | 27.7 | 27.7 | 27.7 | 27.7 | 27.7 | 27.7 |
| Avg. Molecular Wt. of Blend × 1,000 | | | 222 | 150 | 150 | 150 | 250 | 262.5 | 266.1 | 222 | 200.5 | 266.1 |
| % Styrene in Blend | | | 23.3 | 30 | 25 | 15 | 40 | 32.5 | 29 | 27.8 | 27 | 26.6 |
| 100% Modulus-psi | | | 217 | 250 | 225 | 100 | 467 | 300 | 293 | 263 | 250 | 272 |
| Ultimate Tensile Strength-psi | | | 815 | 673 | 693 | 140 | 3450 | 2430 | 2583 | 1338 | 1100 | 1605 |
| Ultimate Elongation-% | | | 637 | 527 | 610 | 457 | 677 | 713 | 740 | 667 | 647 | 720 |
| Alkaline Extraction Nephelos Units | | | 59 | 47 | 49 | 42 | 13 | 3 | 26 | 30 | 42 | 33 |
| Shore "A" Durometer | | | 49 | 55 | 45 | 27 | 80 | 70 | 64 | 55 | 56 | 58 |
| Relative Clarity | | | +3 | +4 | +3 | +2 | +2 | +5 | +4 | +5 | +5 | +4 |

| | | Molec. Wt. × 1,000 | 11 | 12 | 13 | 14 | 15 | 16 | 17 | 18 | 19 | 20 |
|---|---|---|---|---|---|---|---|---|---|---|---|---|
| Radial Block Copolymer | A | 300 | 48 | 33 | 25 | 50 | 33 | | 33 | | | |
| | B | 150 | | | 75 | | | 50 | | | | |
| | C | 150 | | | | | | | | | | |
| | D | 150 | 52 | 67 | | 50 | 67 | 50 | 67 | | | |
| | E | 150 | | | | | | | | 16 | 33 | 16 |
| | F | 250 | | | | | | | | 84 | 67 | 84 |
| Additional Polymers and Additives | | | 27.7 | 27.7 | 27.7 | 27.7 | 27.7 | 27.7 | 27.7 | 27.7 | 27.7 | 27.7 |
| Avg. Molecular Wt. of Blend × 1,000 | | | 222 | 200.5 | 150 | 200 | 217 | 200 | 217 | 234 | 217 | 234 |
| % Styrene in Blend | | | 23.3 | 20 | 32.5 | 35 | 36.7 | 32.5 | 35 | 38 | 31.6 | 35.9 |
| 100 % Modulus-psi | | | 217 | 175 | 283 | 333 | 425 | 237 | 352 | 417 | 293 | 373 |
| Ultimate Tensile Strength-psi | | | 815 | 532 | 707 | 1842 | 3328 | 980 | 2847 | 3358 | 1633 | 3007 |
| Ultimate Elongation-% | | | 637 | 617 | 517 | 650 | 707 | 630 | 713 | 710 | 687 | 713 |
| Alkaline Extraction Nephelos Units | | | 59 | 50 | 40 | 26 | 18 | 37 | 29 | 19 | 39 | 24 |
| Shore "A" Durometer | | | 49 | 41 | 58 | 69 | 77 | 50 | 70 | 77 | 61 | 74 |
| Relative Clarity | | | +3 | +4 | +5 | +4 | +3 | +5 | +4 | +3 | +5 | +3 |

We claim:

1. An unvulcanized radial block copolymer mixture having a high degree of clarity and resealability consisting essentially of (a) from about 10 – 90% by weight of a butadiene-styrene radial block copolymer having a butadiene content in the range of about 85 – 60% by weight and a styrene content in the range of about 5 – 40% by weight, (b) from about 90 – 10% by weight of a butadiene-styrene radial block copolymer having a different butadiene-styrene content in the range of about 85 – 60% by weight and a styrene content in the range of about 15 – 40% by weight and (c) about 5 – 75% by weight of said radial block copolymer mixture of a clear polymeric material selected from the group consisting of polyether and polyester urethane polymers and mixtures of said clear polymeric material, both said radial block copolymers having an average molecular weight of at least 150,000 as measured by inherent viscosity in toluene, wherein said polyether urethane polymers are the reaction products of polyether glycols and aromatic diisocyanates and said polyester urethanes are the reaction products of linear hydroxyl terminated aliphatic polyesters, an aromatic diisocyanate and an aliphatic diol.

2. The radial block copolymer mixture as defined in claim 1 wherein said polymeric material is a thermoplastic polyether urethane polymer.

3. The radial block copolymer mixture as defined in claim 1 wherein said polymeric material is a thermoplastic polyester urethane polymer.

4. The radial block copolymer mixture as defined in claim 1 wherein the amount of butadiene in said (a) portion of said radial block copolymer mixture is 70% by weight and said styrene amount is 30% by weight and wherein the amount of butadiene in said (b) portion of said radial block copolymer mixture is 60% by weight and said styrene is 40% by weight.

5. The radial block copolymer mixture as defined in claim 4 wherein said (a) portion of said radial block copolymer mixture is present in an amount of about 90 – 45% by weight and said (b) portion of said radial block copolymer mixture is present in an amount of about 10 – 55% by weight.

6. The radial block copolymer mixture as defined in claim 4 wherein said (a) portion of said radial block copolymer mixture is present in an amount of about 75% by weight and said (b) portion of said radial block copolymer mixture is present in an amount of about 25% by weight.

7. The radial block copolymer mixture as defined in claim 2 further including a butadient-styrene-methyl methacrylate copolymer.

8. The radial block copolymer mixture as defined in claim 2 wherein said thermoplastic polyether urethane is present in the range of about 10 to about 50 parts by weight per 100 parts by weight of said radial block copolymers.

9. The radial block copolymer mixture as defined in claim 5 wherein said thermoplastic polyester urethane is present in an amount not exceeding about 50 parts by weight per 100 parts by weight of said radial block copolymers.

10. The radial block copolymer mixture as defined in claim 1 further including a plasticizer present in an amount in the range of about 2 to about 50 parts by weight per 100 parts by weight of said radial block copolymers.

11. The radial block copolymer mixture as defined in claim 10 wherein said plasticizer is mineral oil.

12. The radial block copolymer mixture as defined in claim 1 wherein said mixture is molded to form a medical plastic product.

13. The medical plastic product as defined in claim 12 in the form of plastic tubing.

14. The medical plastic product as defined in claim 12 in the form of a drip chamber.

15. The medical plastic product as defined in claim 12 in the form of a reseal device.

16. The medical plastic product as defined in claim 12 in the form of an adapter.

17. The medical plastic product as defined in claim 16 wherein said adapter is a needle adapter.

18. The medical plastic product as defined in claim 12 in the form of a closure.

19. The medical plastic product as defined in claim 18 wherein said closure is a pharmaceutical closure.

20. The medical plastic product as defined in claim 12 in the form of a syringe plunger tip.

21. The medical plastic product as defined in claim 12 in the form of a flexible container.

22. The medical plastic product as defined in claim 12 in the form of an elastomeric bulb.

* * * * *

UNITED STATES PATENT AND TRADEMARK OFFICE
CERTIFICATE OF CORRECTION

PATENT NO. : 4,048,254
DATED : September 13, 1977
INVENTOR(S) : Edward Lawrence Hillier, et al.

It is certified that error appears in the above-identified patent and that said Letters Patent are hereby corrected as shown below:

In Column 11, line 10, Claim 1: please delete "-styrene"

so that line 10 reads:

different butadiene content in the range of

Signed and Sealed this

Twenty-first Day of February 1978

[SEAL]

Attest:

RUTH C. MASON
Attesting Officer

LUTRELLE F. PARKER
Acting Commissioner of Patents and Trademarks